(12) United States Patent
Olsson

(10) Patent No.: US 7,844,428 B2
(45) Date of Patent: Nov. 30, 2010

(54) METHOD FOR ASSESSING LIFE-AFFECTING DAMAGE ON A ROTARY MEMBER

(75) Inventor: Karl-Erik Olsson, Lönsboda (SE)

(73) Assignee: Volvo Construction Equipment AB, Carl Lihnells Vag, Braas (SE)

( * ) Notice: Subject to any disclaimer, the term of this patent is extended or adjusted under 35 U.S.C. 154(b) by 1293 days.

(21) Appl. No.: 10/707,781

(22) Filed: Jan. 12, 2004

(65) Prior Publication Data

US 2005/0021320 A1 Jan. 27, 2005

Related U.S. Application Data

(63) Continuation of application No. PCT/SE02/00879, filed on May 7, 2002, now abandoned.

(30) Foreign Application Priority Data

Jul. 10, 2001 (SE) .................................... 0102479

(51) Int. Cl.
    *G06G 7/48* (2006.01)
(52) U.S. Cl. .................................... 703/7; 703/6; 703/8
(58) Field of Classification Search ...................... 703/6, 703/7, 8
    See application file for complete search history.

(56) References Cited

U.S. PATENT DOCUMENTS

| 5,019,760 A | 5/1991 | Chu et al. |
| 5,723,779 A | 3/1998 | Hara et al. |

OTHER PUBLICATIONS

Fatemi et al., "Cumulative Fatigue Damage and Life Prediction Theories: A Survey of the State of the Art for Homogeneous Materials", International Journal of Fatigue, Jan. 1998, pp. 9-34.*
Lauster et al., "Thermic Computations in Multiple-Disk Clutches", translated into English by USPTO from "Waermetechnische Berechnungen bei Lamellenkupplungen", VD1-Z 115 (1973), pp. 122-126.*
Steinhilper, "The Time-Temperature Progression in Fast-Shifting Friction Clutches and -Brakes", translated into English by USPTO from "Der zeitliche Temperaturverlauf in schnellgeschalteten Reibungskupplungen und -bremsen", Diss. T, H. Karlsruhe 1962. ATZ Bd. 65 (1963) S. 223/29 and 326/29.*

(Continued)

*Primary Examiner*—Kamini S Shah
*Assistant Examiner*—Herng-Der Day
(74) *Attorney, Agent, or Firm*—Novak Druce + Quigg LLP

(57) ABSTRACT

Method and arrangements for predicting life-affecting damage on a rotary member subjected to repeated loading during operation. A number of operating parameters are measured, and a temperature increase during each loading is calculated from the operating parameters. More precisely, a total temperature in a part of the rotary member is calculated for each loading by summation of basic temperature of the rotary member before the loading concerned and the temperature increase, and the values for the total temperature are used as a measure of the damage. The part of the rotary member for which the total temperature is calculated defines a surface that is acted on when the rotary member is loaded. Two sets of predetermined functions (M, N), which each comprise at least one function, are used for temperature-increase calculation, and the set which is used for temperature-increase calculation is selected depending on at least the nature of the rotary member.

15 Claims, 3 Drawing Sheets

OTHER PUBLICATIONS

Lauster VDI, Von Eugene; Staberoh, Uwe "Warmetechnische Berechnungen bei Lamellenkupplungen" (1973) VDI-Z 115.

Kruger, H. "Das Temperaturverhalten der nassen Lamellenkupplungen" (1963) Konstruktion 17.

Tataiah, K. "An Analysis of Automatic Transmission Clutch-Plate Temperatures" SAE 720287 (1972).

Young, W.C.; Budynas, R.G. "Roark's Formulas for Stress and Strain" 7th Edition (2002) McGraw-Hill.

Sun, J.Q.; Wang, X. "Fatigue Analysis of Non-Linear Structures with Von Mises Stress" Journal of Sound and Vibration 245(5); (2001) 947-952.

Sarkani, S.; Michaelov, G. "NonLinear Damage Accumulation In Stochastic Fatigue of FRP Laminates" 8th ASCE Specialty Conference on Probabilistic Mechanics and Structural Reliability; PMC2000-302; 1-6.

* cited by examiner

METHOD FOR ASSESSING LIFE-AFFECTING DAMAGE ON A ROTARY MEMBER

CROSS REFERENCE TO RELATED APPLICATIONS

The present application is a continuation patent application of International Application No. PCT/SE02/00879 filed 7 May 2002 which was published in English pursuant to Article 21(2) of the Patent Cooperation Treaty, and which claims priority to Swedish Application No. 0102479-3 filed 10 Jul. 2001. Both applications are expressly incorporated herein by reference in their entireties.

BACKGROUND OF INVENTION

1. Field of the Invention

The present invention relates to a method for assessing life-affecting damage on a rotary member that is subjected to repeated loading during operation. The method includes measuring a number of operating parameters and calculating a temperature increase during each loading from the operating parameters. A total temperature in a part of the rotary member is calculated for each loading by summation of a basic temperature of the rotary member before the loading concerned, and the temperature increase, and the values for the total temperature are used as a measure of the damage.

The present invention relates to a method for assessing life-affecting damage on a rotary member that is subjected to repeated loading during operation. The method includes measuring a number of operating parameters and calculating a temperature increase during each loading from the operating parameters. A total temperature in a part of the rotary member is calculated for each loading by summation of a basic temperature of the rotary member before the loading concerned, and the temperature increase, and the values for the total temperature are used as a measure of the damage.

The invention can be applied in, for example, a means of transport, such as a vehicle, a craft or other transport-types of equipment such as rail-mounted transport means. Application may also be made in such land vehicles, such as vehicles having wheels or caterpillar tracks. The invention is in particular suitable for application in a construction machine, such as a wheel loader, excavating machine or a frame-steered or articulated vehicle, also referred to as a dumper. The area of application of the invention is nevertheless not limited to these applications, and it can also be applied in stationary arrangements.

2. Background Art

U.S. Pat. No. 5,723,779 describes a system for producing an indication of the remaining life of a friction clutch. It is assumed that the temperature of the clutch disk is a decisive parameter for its life. The temperature of the clutch disk is determined by summation of a temperature increase on activation of the clutch and the basic temperature of the clutch disk before activation of the clutch. These two values are therefore added, and a measure of the temperature of the clutch disk during activation is obtained. A large number of parameters are measured for the calculation: speed difference in the clutch, pressure of the oil supplied to the piston that brings about engagement of the clutch, and loading time. The temperature of the coolant of the clutch is also measured. This temperature is used as a measure of the basic temperature of the clutch disk before every brake application.

However, it has become apparent that it would be desirable to have a method for assessing consumed life, which provides a more accurate result compared with the system according to U.S. Pat. No. 5,723,779.

It may furthermore be mentioned that methods are available for accurate calculation of temperature distribution in a loaded rotary member, such as FEM (Finite Element Methods). However, such methods require great computer power and take a relatively long time, which makes them less suitable for certain applications, such as in high-frequency measurement, calculation and logging of data, and especially when the calculation is to be performed in a computer in a vehicle.

SUMMARY OF INVENTION

One object of the invention is to provide a method that yields an accurate assessment of damage caused in a rotary member that is loaded in operation in an effective manner in terms of computer capacity.

This object is achieved by virtue of the fact that that part of the rotary member for which the total temperature is calculated defines a surface that is acted on when the rotary member is loaded. Two sets of predetermined functions, which each comprise at least one function, are used for temperature-increase calculation. The set used for temperature-increase calculation is selected depending on at least the nature of the rotary member.

The surface temperature of a rotary member in the form of, for example, a brake disk constitutes a good measure of damage/wear to the disk. On the basis of surface-temperature changes, the remaining life of the disk can be calculated.

It has been found that the total temperature of the rotary member can be described in a very accurate manner with only the two sets of functions. In this way, opportunities are afforded for calculating and logging, in an effective manner in terms of time and computer capacity, the values for calculating damage caused/life consumed.

Characteristics of the rotary member are determined, at least in part, based on the member's internal structure, external dimensions, the material of its construction, the material properties and the thickness of the rotary member. According to the embodiment described below, the function used for temperature-increase calculation is selected depending not only on the nature of the rotary member, but also on the duration in time of the loading.

According to a preferred embodiment of the invention, the time for which the rotary member is applied is measured, and the set of functions used for each specific temperature-increase calculation is also selected depending on this time. More precisely, a constant is calculated after every loading on the basis of both the nature of the rotary member and the loading time. When a calculated value of the constant lies below a predetermined limit value, a first set of functions is used, and when a calculated value lies above the limit value, a second set of functions is used. It has been found that it is possible to define the temperature-change characteristic of the rotary member very accurately with the sets of functions in a simple manner which is effective in terms of computer capacity. In other words, the limit value is used to define which function is to be used, and the calculation is then performed with the selected function.

According to another preferred embodiment of the invention, the specific function that is used for temperature-increase calculation is selected from a specifically selected set of functions depending on loading type. Loading type means the shape of the loading, which may be, for example, triangular or rectangular. From the measured operating parameters, the loading type is therefore defined first, after which a function belonging to the specific loading type is selected. In this way, it is possible to calculate the temperature increase with great accuracy.

According to another preferred embodiment of the invention, each of the sets comprises only one function, which is thus selected irrespective of loading type. In this way, the temperature increase can be calculated in an effective manner in terms of computer capacity.

According to another preferred embodiment of the invention, each of the graphs of the functions has such a shape that a logarithmic first expression for the temperature increase changes linearly as a function of a logarithmic second expression for the nature of the rotary member and the duration in time of the loading. More precisely, the second expression is calculated as a power function of the duration in time of the loading divided by a value for the nature of the rotary member. This calculation of the temperature increase affords opportunities for a very accurate value of damage caused/life consumed by each cycle of loading to be determined.

According to another preferred embodiment of the invention, the total temperature value produced, or a converted damage value, for each loading instance is stored in a position in a memory, which position defines a specific temperature range or damage range. In this way, opportunities are afforded for using the part damage theory. More precisely, the damage or consumed life is calculated on the basis of the number of times each specific range has been reached and knowledge of the damage durability of the rotary member.

According to another preferred embodiment of the invention, the time between two successive loading cycles is measured, and a new basic temperature for the later loading is determined with the aid of the measured time. In this way, opportunities are afforded for taking into account what happens to the rotary member between two loadings. More precisely, the new basic temperature for the later loading is calculated with an expression for a cooling process of the rotary member after the preceding loading has ended. This results in increased accuracy in the calculation method.

Traditionally, calculation of the surface temperature of the disk has been based on measurements of the temperature of the cooling oil supplied to the disk. A disadvantage of using the cooling-oil temperature for calculating the surface temperature is that this is a relatively inaccurate measure of the surface temperature, especially when loading of the disk has just ended and also when operation of the brake that includes the disk begins.

BRIEF DESCRIPTION OF DRAWINGS

The invention will be described in greater detail below with reference to the embodiments shown in the accompanying drawings, in which.

DETAILED DESCRIPTION

Figure 1:
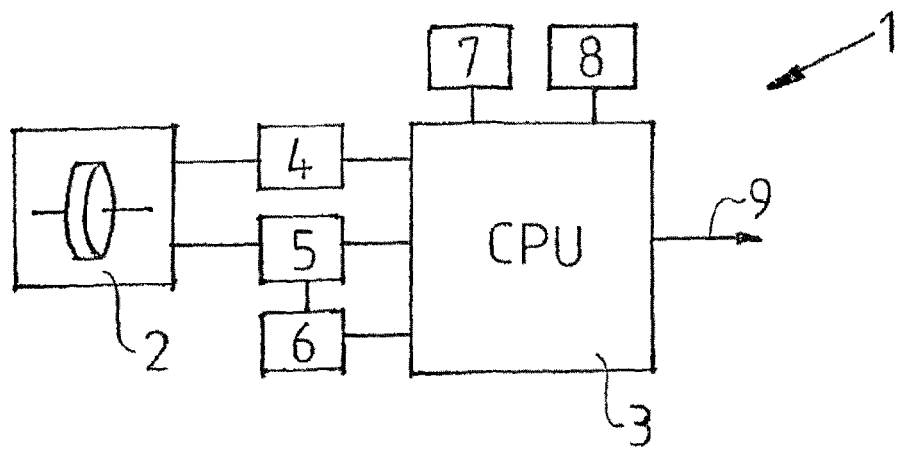
FIG. 1 shows a block diagram of a system for implementing the method according to the invention.

FIG. 1 diagrammatically shows in block format a system 1 for implementing a method for assessing damage to, or consumed life of, a member 2 intended for rotation and having surfaces subjected to friction. In the description below, the rotary member 2 is exemplified by a brake disk for the purpose of facilitating understanding of the disclosure. It is assumed that the temperature changes in the brake disk during brake applications have decisive significance for the disk's life. By means of the method below, consumed life of the brake disk is therefore predicted on the basis of these temperature changes.

The damage to the brake disk is described by means of an approximate description of the dependence of the surface temperature on measured data. Each brake application produces a temperature cycle of the brake disk. As described further below, the life of the brake is described by the number of surface-temperature cycles in the form of a power function (FIG. 5) in an analogous manner to the S/N curve obtained in the case of fatigue.

With the aid of a part damage theory, the damage durability consumed by the braking cycles in relation to damage durability obtained from tests is then calculated.

The system 1 comprises (includes, but is not limited to) a control unit (CPU) 3 and, connected operationally to this, a first sensor 4 for detecting the rotational speed of the brake disk 2, a second sensor 5 for detecting a pressure applied to the brake disk or a force in order to activate the brake disk, and a third sensor 6 for detecting the time for which the brake disk is applied.

The measurements of the operating parameters are performed at predetermined time intervals. The time intervals are sufficiently small that a large number of measurements will be made during each loading. The intervals between the measurements can also be different during loading and during the time between two loadings. The intervals between the measurements can, for example, be smaller during loading than when the rotary member is in an unloaded state.

The system 1 also comprises means 7, connected to the control unit 3, for calculating a total temperature on the surface of the brake disk 2 and also means 8 for storing calculated data. The total temperature is referred to below as surface temperature for the purpose of facilitating understanding of the text.

The control unit 3 delivers an output signal 9 with a value of the damage caused to the disk during operation or the consumed life of the brake disk 2.

According to a method of the invention, a maximum temperature on the surface of the brake disk 2 is calculated by summing a basic temperature before a brake application with a temperature increase during the brake application. A description is given below of, first, calculation of a maximum temperature increase on the surface and, then, calculation of the basic temperature for a subsequent brake application. The total temperature in that part of the rotary member that defines a friction surface is repeatedly calculated.

Calculation of Temperature Increase: According to the present invention, a value for what is known as a Fourier constant, Fo, is calculated first. This Fourier constant is dependent on the material thickness and other, heat-related attributes or characteristics of the brake disk, and also the time for which the brake disk is activated. More precisely, the Fourier constant, Fo, is calculated as follows:

$$Fo = 4*\alpha*t/S^2, \text{ where}$$

$\alpha = \lambda/(\rho*c) =$ the thermal diffusivity constant
$\lambda =$ thermal conductivity
$\rho =$ density
$c =$ heat capacity
$t =$ time the disk is applied
$S =$ thickness of disk According to a first embodiment of the invention, one of two different functions K, L (See FIG. 2) is selected on the basis of the Fourier constant calculation. Each of the functions is described by a straight line in the diagram. The two linear functions have different slope coefficients and intersect one another. With the aid of the function selected, an expression for the temperature increase is obtained. More precisely, the diagram has the Fourier constant on the x-axis and the expression for the temperature increase on the y-axis. Both the x-axis and the y-axis have logarithmic scales. In the specific embodiment, the first function K is used when Fo is less than 0.5 and the second function L when Fo is greater than 0.5. Because the functions intersect, either function could be used with the same result in the event Fo is equal to 0.5, which is where the functions intersect.

The temperature increase is then calculated from the expression for the temperature increase.

Figure 2:
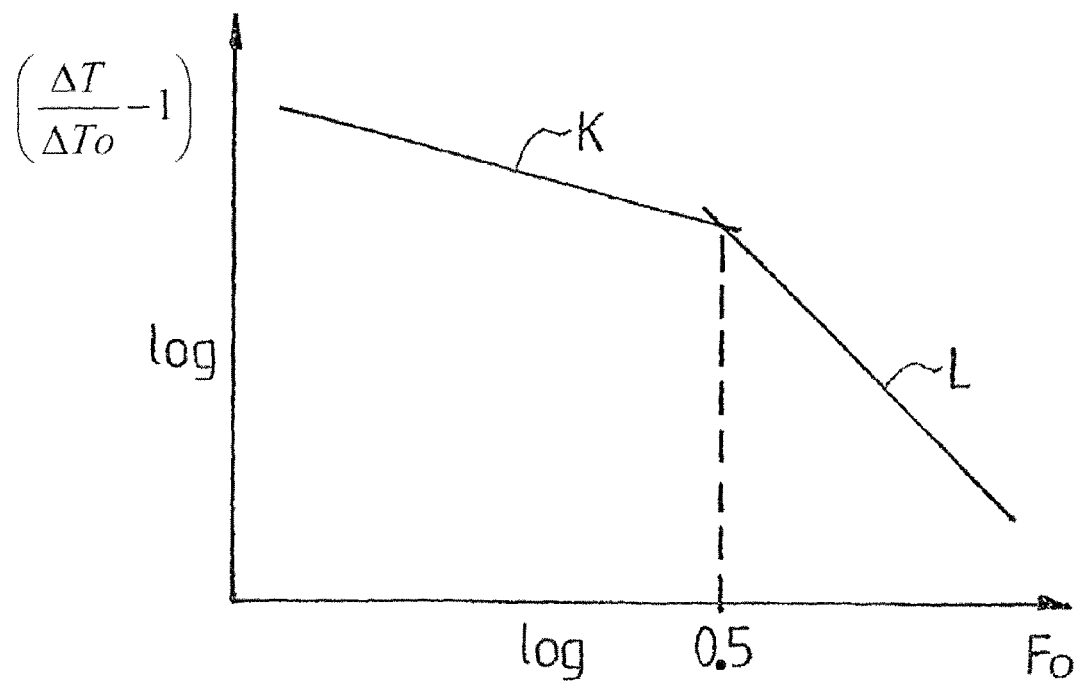
FIG. 2 shows two graphs for two functions that are used in calculating the temperature increase according to a first embodiment.

The two linear functions K and L in FIG. 2 are produced in the following way:

From reference [1], an expression is previously known for calculating a maximum temperature increase $\Delta T$ on the surface.

$$\Delta T = \Delta To(1 + 0.15 * Fo^{-1.9}) \quad (1)$$

$$\Delta To = 2*E/(\rho*c*S), \text{ where}$$

$E =$ energy of the thermal pulse
$\rho =$ density
$c =$ heat capacity
$S =$ thickness of disk This applies for a triangular thermal pulse on the disk.

From reference [2], an expression is derived for the surface temperature increase in the case of a rectangular thermal pulse. In an analogous manner to calculation (1) above, this can be converted to:

$$\Delta T = \Delta To(1 + 1/(3*Fo)) \quad (2)$$

The functions (1) and (2) apply when Fo is greater than 0.5.

According to the first preferred embodiment of the invention, fitting was carried out of the curves for the two functions (1) and (2) and also the values from FEM calculations performed. The curve fitting showed that the maximum temperature increase $\Delta T$ on the surface can be described with great accuracy with a power function, namely the function L. This function can generally be expressed as follows:

$$A = B*(t/to)^q \quad (3)$$

where $t/to = Fo$, with t being equal to the duration of the thermal pulse and to, which is equal to $S^2/(4*\alpha)$, being a constant characteristic of the disk.

B and q are constants that express the position and the slope of the curve, respectively. A is an expression for the temperature increase according to the following:

$$\Delta T/\Delta To - 1 = 1/A \quad (4)$$

The specific expression for the function for the fitted curve L can be produced with known curve-fitting methods. This expression is therefore used as a function for calculating the maximum temperature increase $\Delta T$ on the surface when Fo is greater than 0.5.

From references [1] and [3], it is possible to obtain from the diagram parameter values for a corresponding formula when Fo is less than 0.5. In other words, the function (3) applies with other constants B and q when Fo is less than 0.5.

Fitting was carried out of the parameter values produced and also the values from FEM calculations performed. This curve fitting also showed that it is possible to describe the maximum temperature increase $\Delta T$ on the surface with great accuracy with the linear function K for Fo less than 0.5.

The two linear functions K, L produced proved to give great accuracy in the calculation of the maximum temperature increase $\Delta T$ on the surface. The calculations can moreover be performed in an effective manner in terms of computer capacity.

Figure 3:
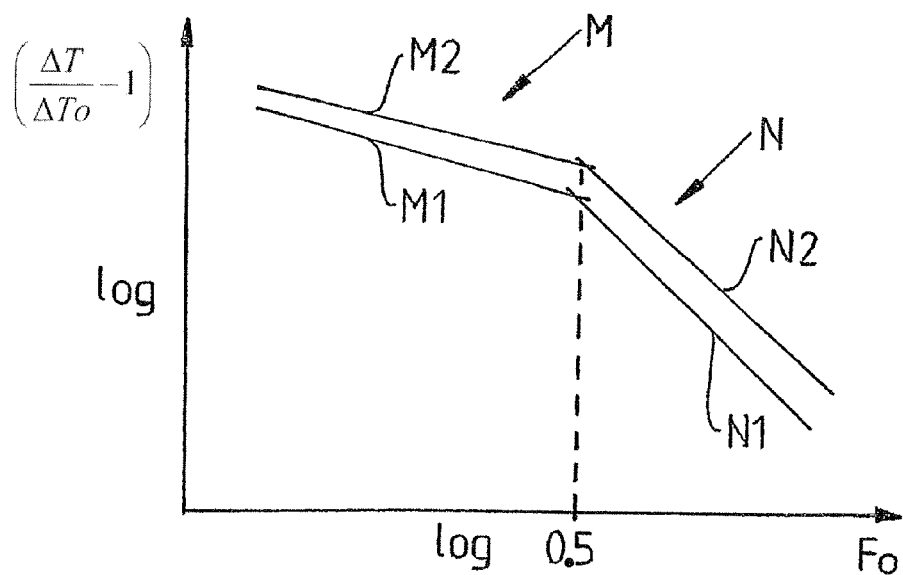
FIG. 3 shows four graphs for two sets with two functions each which are used in calculating the temperature increase according to a second embodiment.

In the abovementioned total appraisal or curve fitting of the function, adjustment for triangular load or for rectangular load in determining the functions K and L is not carried out. According to a second preferred embodiment of the invention, in contrast, use is made of a first set M of two functions M1, M2 when Fo is below a specific limit value and a second set N of two functions N1, N2 when Fo is above this specific value (FIG. 3). The two functions in each of the sets M, N correspond to different loading types. More precisely, the functions M1 and N1 pertain to a rectangular load, and the functions M2 and N2 pertain to a triangular load.

The type of load shape being applied to the brake disk is determined on the basis of measured operating parameters. The first function M1 and, respectively, N1 are used if being applied to a rectangular load, and the second function M2 and, respectively, N2 are used if being applied to a triangular load. The limit value used for Fo is 0.5 in this case as well. Thus, for rectangular loading, the function M1 is used if Fo is less than 0.5, whereas the function N1 is use if Fo is greater than 0.5. Because the functions M1 and N1 intersect, either function could be used with the same result in the event Fo is equal to 0.5, which is where the functions intersect. Similarly, for triangular loading, the function M2 is used if Fo is less than 0.5, whereas the function N2 is use if Fo is greater than 0.5. Because the functions M2 and N2 intersect, either function could be used with the same result in the event Fo is equal to 0.5, which is where the functions intersect.

Loading shape: To determine loading type, the rotational speed (v) of the brake disk 2, the pressure (p) applied, and the time (t) for which the brake disk is applied are measured by means of the sensors 4-6. With the aid of the values measured in this way, the energy (E) in a brake application is calculated according to:

$$E = \Sigma(k*p*v*dt) \quad (5)$$

where k is a proportionality constant.

For what is known as a triangular load, $E = Pmax*t/2$, and for a rectangular load, $E = Pmax*t$, where Pmax is the maximum power and t is the braking time. $E/(Pmax*t)$ is therefore calculated, which provides a measure of the shape of the loading. The calculated value $E/(Pmax*t)$ is compared with a limit value; if the calculated value lies above the limit value, the load type is considered to be rectangular, and if the calculated value lies below the limit value, the load type is considered to be triangular. The limit value is selected in the time range 0.5-1.0, and suitably the value 0.8 is selected. The value 0.5 corresponds to a pure triangular pulse, and the value 1.0 corresponds to a pure rectangular pulse. Use is then made of the function that corresponds to the value worked out.

Figure 4:
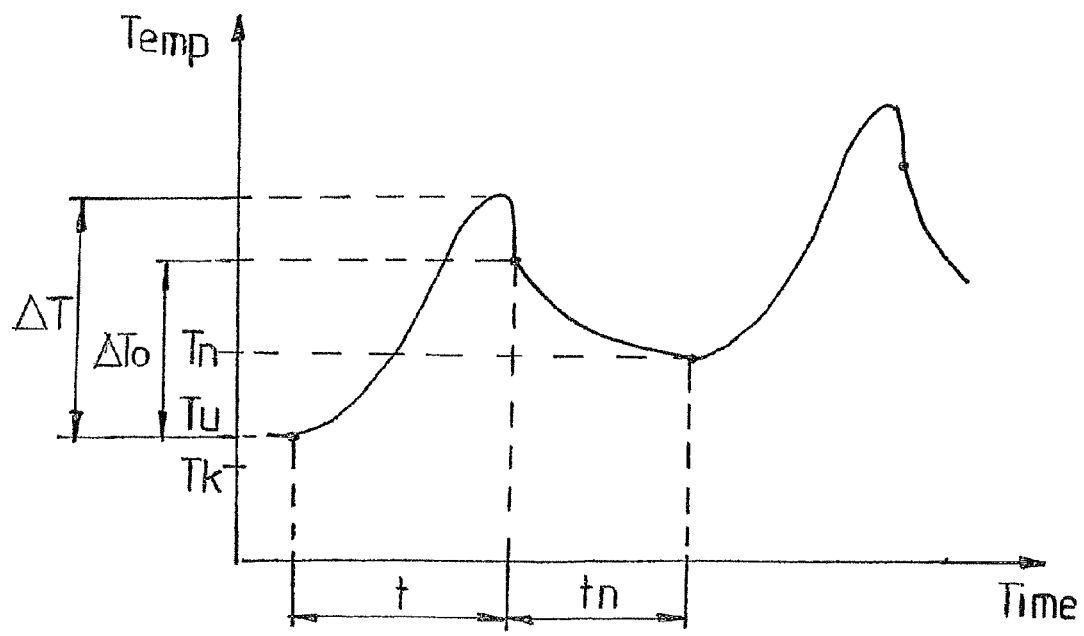
FIG. 4 shows a graph of the surface temperature of the brake disk as a function of time in the case of two brake applications.

Calculation of the Basic Temperature: According to the invention, an estimate is made of the temperature on the surface of the brake disk immediately before the next braking begins. This is explained below with reference to FIG. 4. The starting point is the calculated final temperature of the surface of the brake disk after a brake application. The time until the next brake application is measured and, via an estimate of the cooling process, the basic temperature for the next brake application is calculated.

From an initial temperature Tu (FIG. 4), we have a surface temperature Tu+ΔT on the brake disk immediately after braking. However, the temperature in the disk is evened out quickly to Tu+ΔTo, which represents the temperature at which the cooling process begins. The temperature difference between the brake disk and its environment when cooling begins is therefore Tu+ΔTo−Tk, where Tk is the temperature of the cooling element. If the time until the next braking is tn, we have the temperature Tn when the next braking begins.

$$Tn = Tk + (Tu + \Delta To - Tk) * \exp(-tn/kt) \quad (6)$$

Where kt=m*c/(K*A)=the time constant for the cooling process, which is known.

K=the cooling constant W/(m2*K)
A=the cooling area
m=the mass

ΔTo has been calculated with the functions described above in connection with FIGS. 2 and 3. Time measurement gives the time tn, which allows calculation of Tn because other parameters are known. The calculated value Tn constitutes the basic temperature for the next brake application.

In order to reduce the risk of the calculated initial temperature Tu (and thus the maximum surface temperature calculated on the basis of the initial temperature) increasing unlimitedly as a consequence of an incorrectly selected constant or the like in the calculation, it is proposed that the temperature of the coolant is measured in a relatively long interval between two brake applications and that this value is used as a new initial temperature for the temperature calculation for the later brake application. Here, it is assumed that, in the relatively long time interval, the brake disk has approximately the same temperature as the coolant.

Total Surface Temperature: By summing the value worked out for the basic temperature with the calculated temperature increase for subsequent brake application, a value is obtained for a maximum total temperature. In this way, increased accuracy is obtained, especially in the case of repeated brake applications with such small mutual separations in time that the disk does not have time to return to its previous basic temperature between brake applications.

Logging of Data: In a matrix in the memory of the system, the number of times the surface temperature of the brake disk reaches each of a large number of specific, predetermined temperature ranges is stored (or logged). In other words, the number of braking cycles that reach different energy levels is stored. Generally, it can be that the number of braking cycles is stored in classes that correspond to different energy, damage and/or temperature ranges.

Figure 5:
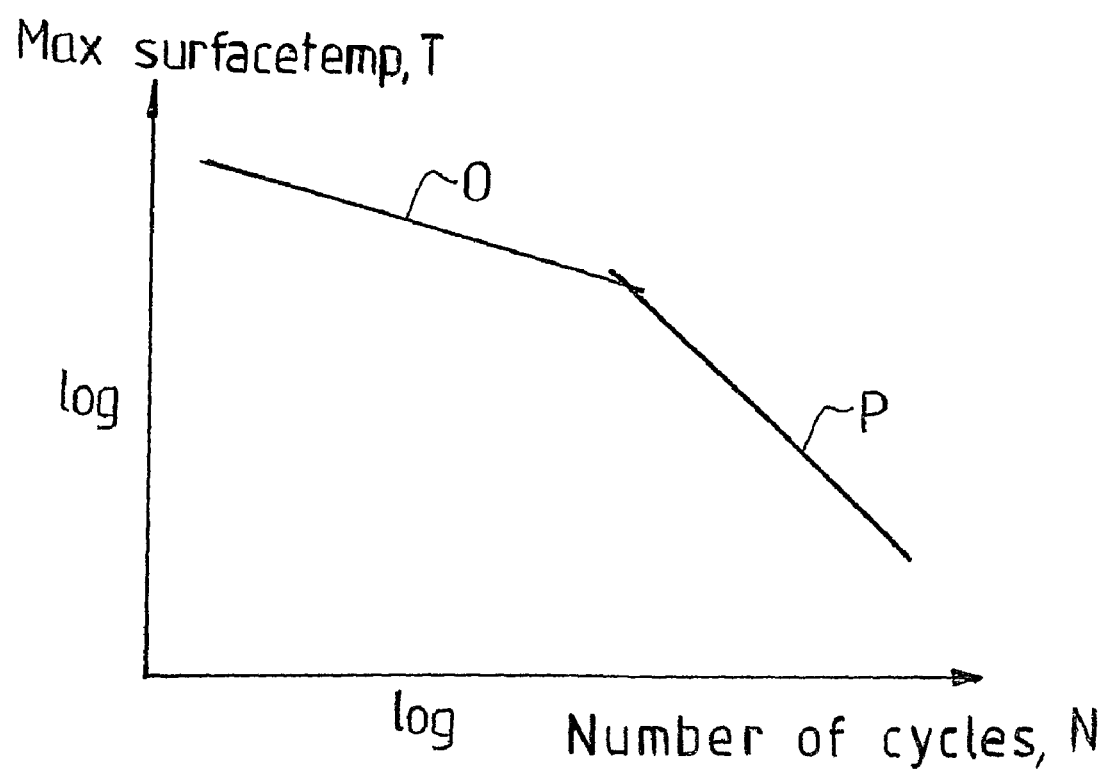
FIG. 5 shows a relationship between maximum surface temperature and the number of loading cycles in a diagram.

Calculation of Remaining/Consumed Life: FIG. 5 shows a relationship between maximum total temperature and number of braking cycles for wearing-out using log-log scales. The relationship consists of two linear functions O, P with different slopes. The reason why two curves are used is that the lining on the brake disk is broken down at high temperature and has a tendency to char. This is because, at high temperatures for linings made of paper, a chemical process, carbonization, takes place. The upper curve O, on the left in the figure, describes the strength in a brake disk, the lining of which has reached such a high temperature that charring has started.

The slope of the curves and the break-point between the upper curve O and the lower curve P are obtained from rig testing. The slope of the left, upper curve O may, however, be difficult to produce with great accuracy and, in such a case, it can be estimated with, for example, the Arrhenius function.

A value for initial life of the rotary member is therefore calculated by means of real tests carried out, and this value is used for calculating the remaining life.

The strength of the brake disk is described by $$T^{m1} * N = C1; \text{ therefore, } N = C1/T^{m1} = C1 * T^{-m1} \text{ (applies for curve P)}$$

$$T^{m2} * N = C2; \text{ therefore, } N = C2/T^{m2} = C2 * T^{-m2} \text{ (applies for curve O)}$$

where
T is maximum surface temperature,
N is the number of braking cycles, and
m1, m2, C1, C2 are parameter values determined from rig testing.

Under a linear part damage theory (Palmgren-Miner), total accumulated damage D to any given point in time may be expresses as the sum, over all encountered loading ranges, of partial damage n/N accumulated within each loading range, i.e., D=Σn/N. Therefore, substituting the expressions above for N into that expression, two accumulated damage values D1 and D2 can be expressed as are evaluated from the measurements $$D1 = \Sigma n_1/(C1 * T^{-m1}) = \Sigma n_1 C1^{-1} * T^{m1} = C1^{-1} * \Sigma n_1 * T^{m1}$$
(applies for the curve P)

$$D2 = \Sigma n_2/(C2 * T^{-m2}) = \Sigma n_2 C2^{-1} * T^{m2} = C2^{-1} * n_2 * T^{m2}$$
(applies for the curve O)

where
T is maximum surface temperature,
D is damage value per unit of time or distance (damage per hour or damage per kilometer), and n1 and n2 are the number of braking cycles per temperature level and unit of time or distance.

The part damage value d=L*D1/C1+L*D2/C2
Where L is the use time L=d/(D1/C1+D2/C2)
If, for wearing-out, it is considered that the part damage value is d=1, then $$\text{Life} = 1/(D1/C1 + D2/C2)$$

is obtained.

It is also possible to calculate the remaining use time La as follows: the use time L and the corresponding part damage value are known according to the above. If it is assumed that the part damage is d=1 for a worn-out component, $$Lå = L * (1-d)/d$$

is obtained.

It may also be mentioned that there is no break-point for some types of lining, which of course simplifies the calculations above somewhat.

The invention is not to be regarded as being limited to the illustrative embodiments described above, but a number of further variants and modifications are possible within the scope of the patent claims.

For example, the assessment of damage/consumed life described above can be carried out for crack formation in brake disks or linings. Cracked brake disks are a not unfamiliar phenomenon. There is a close connection between stresses/strains and temperature and gradients. As we are measuring temperature and number of braking cycles, we have a basis for predicting the time of initiation and growth of cracks in disks and plates. This presupposes, like the case for wear, that we have carried out rig tests that describe the relationship between temperature cycles and crack formation. This can also be described with power functions and thus be handled in an analogous manner to wear as above. An example of calculation of crack formation in brake disks or linings is described below.

The surface of a solid body suddenly undergoes a temperature increase dT, which results in a compressive stress, St, on the surface which, according to reference [4], is $$St = dT*\alpha*E/(1-\nu)$$

Where $\alpha$ = the thermal expansion constant (1/degree)
E = the modulus of elasticity
$\nu$ = Poisson's constant As can be seen, the stress is linear with the temperature increase. Even though crack formation is much more complex, for example the thermal expansion on the surface plasticizes parts which, after cooling, are affected by tensile stresses, an indication is nevertheless obtained that the stress level is related to temperature increases and gradients. Crack formation and growth are, as known, related to stress variation.

Consequently, it is possible to determine with rig tests a relationship between the maximum surface temperature and the number of braking cycles for cracks in a disk or lining. This produces Wöhler curves (S/N curves or, more correctly, T/N curves) in an analogous manner to those used above for determining time until wearing-out.

At high temperatures, the strains can be so great that we obtain different slopes in the Wöhler diagram. By introducing one or more break-points, these problems can also be handled in an analogous manner to the breakpoint method in the wear case.

To sum up, it is therefore possible to handle the crack problem in an entirely analogous manner to the wear problem.

According to another example, the assessment of damage/consumed life described above can be performed for a gearwheel in a gear train. A certain wear phenomenon on gears can be treated using the same model as was used above for brakes. Such wear occurs in connection with transmission of relatively great torques at high sliding speeds. The critical problem consists in carrying away sufficiently rapidly the heat generated in the engagement by the friction. The problem is therefore analogous to the problem we solved for brakes. The damage durability is obtained from rig tests. Time-integrated torque and speed provide a measure that is proportional to the energy developed in the contact surfaces. Periods with high torques/speeds can be regarded like the braking cycles as above. More precisely, the oil film between two contact surfaces can be broken down at high loads, which produces considerable tooth wear. The time between loadings is the time it takes for a gearwheel contact surface intended for engagement to move to the next engagement instance.

The following background documents are hereby expressly incorporated for purposes of disclosure in the present application, and for reference by concerned persons skilled in the relevant art:

[1] Lauster, E. and Staberoh, U. "Wametechnische Berechnungen bei Lamellenkupplungen" VDI-Z 115 (1973);

[2] Kruger, H. "Das Temperaturverhalten der nassen Lamellenkupplungen" Konstruktion 17 (1963);

[3] Tataiah, K. "An Analysis of Automatic Transmission Clutch-Plate Temperatures" SAE 720287;

[4] Roark, Raymond J. "Formulas for stress and strain."

The invention claimed is:

1. A method for assessing heating-induced, life-affecting damage to a rotary member that is subjected to cyclical, heat-generating loading, said method comprising:
  a) calculating a heating parameter that is based on the thermal diffusivity constant $\alpha$ of the rotary member and the length of time for which the rotary member is subject to a given cycle of heat-generating loading, where $\alpha = \lambda/(\rho*c)$, $\lambda$, is the thermal conductivity of the rotary member, $\rho$ is the density of the rotary member, and c is the heat capacity of the rotary member;
  b) selecting a function and calculating a maximum temperature associated with the rotary member for the given cycle of heat-generating loading using the selected function, wherein one function is selected if the heating parameter is less than a predefined limit value; wherein another function is selected if the heating parameter is greater than said predefined limit value, said another function intersecting said one function at said predefined limit value; and wherein either said one function or said another function is selected if the heating parameter is equal to said predefined limit value;
  c) repeating steps a) and b) over the course of a multitude of heat-generating loading cycles;
  d) tabulating the number of heat-generating loading cycles which have occurred in each of a plurality of pre-defined temperature categories, wherein each of said pre-defined temperature categories corresponds to a range of maximum temperatures that may be generated in association with the rotary member in any given cycle of heat-generating loading; and
  e) using the tabulated number of heat-generating loading cycles which have occurred in each of said plurality of pre-defined temperature categories and using pre-established, heating-related life expectancy information for said rotary member, assessing a cumulative amount of heating-induced damage which has occurred to said rotary member using a partial damage theory;
  wherein said steps a) through e) are executed automatically on electronic computing means and wherein said method further comprises outputting from said electronic computing means a signal that is indicative of the cumulative amount of heating-induced damage which has occurred to said rotary member.

2. The method of claim 1, wherein said heating parameter is a Fourier constant Fo, with $Fo = 4*\alpha*t/S^2$, where t is the length of time for which the rotary member is subject to the given cycle of heat-generating loading and S is the thickness of the rotary member.

3. The method of claim 1, wherein the maximum temperature associated with the rotary member calculated in said step b) is a surface temperature of the rotary member.

4. The method of claim 1, wherein said one function in said step b) is selected from a first set of functions, with a first function in said first set of functions corresponding to loading cycles having a first type of loading profile and with a second function in said first set of functions corresponding to loading cycles having a second type of loading profile, and wherein said another function in said step b) is selected from a second set of functions, with a first function in said second set of functions corresponding to loading cycles having said first type of loading profile and with a second function in said second set of functions corresponding to loading cycles having said second type of loading profile.

5. The method of claim 4, wherein each of the functions in said first set of functions and each of the functions in said second set of functions is linear when depicted on a logarithmic-by-logarithmic graph with the logarithm of a heating-related quantity depicted as a function of the logarithm of said heating parameter.

6. The method of claim 1, wherein said one function and said another function are each linear when depicted on a logarithmic-by-logarithmic graph with the logarithm of a heating-related quantity depicted as a function of the logarithm of said heating parameter.

7. The method of claim 1, wherein the maximum temperature is calculated in said step b) as the sum of a first addend that is a base temperature of the rotary member and a second addend that is a temperature rise associated with the given cycle of heat-generating loading.

8. The method of claim 7, wherein the selected function is used to calculate the second, temperature rise addend.

9. The method of claim 7, wherein said base temperature is calculated by accounting for cooling of the rotary member between the end of the heat-generating loading cycle that immediately precedes said given heat-generating loading cycle and the beginning of said given heat-generating loading cycle.

10. The method of claim 1, wherein said rotary member is disk in a clutch or a brake.

11. The method of claim 1, wherein said rotary member is a gearwheel in a gear train.

12. The method of claim 1, wherein said signal that is indicative of the cumulative amount of heating-induced damage which has occurred to said rotary member specifies the amount of damage that has occurred to said rotary member.

13. The method of claim 1, wherein said signal that is indicative of the cumulative amount of heating-induced damage which has occurred to said rotary member specifies the amount of life remaining in said rotary member.

14. A computer program product comprising program segments which, when run on electronic computing means, execute the following steps:
a) calculating a heating parameter that is based on the thermal diffusivity constant $\alpha$ of the rotary member and the length of time for which the rotary member is subject to a given cycle of heat-generating loading, where $\alpha = \lambda/(\rho^* c)$, $\lambda$ is the thermal conductivity of the rotary member, $\rho$ is the density of the rotary member, and c is the heat capacity of the rotary member;
b) calculating a maximum temperature associated with the rotary member for the given cycle of heat-generating loading, wherein the maximum temperature is calculated using one function if the heating parameter is less than a predefined limit value; using another function if the heating parameter is greater than said predefined limit value, said another function intersecting said one function at said predefined limit value; and using either said one function or said another function if the heating parameter is equal to said predefined limit value;
c) repeating steps a) and b) over the course of a multitude of heat-generating loading cycles;
d) tabulating the number of heat-generating loading cycles which have occurred in each of a plurality of pre-defined temperature categories, wherein each of said pre-defined temperature categories corresponds to a range of maximum temperatures that may he generated in association with the rotary member in any given cycle of heat-generating loading;
e) using the tabulated number of heat-generating loading cycles which have occurred in each of said plurality of pre-defined temperature categories and using pre-established, heating-related life expectancy information for said rotary member, assessing a cumulative amount of heating-induced damage which has occurred to said rotary member using a partial damage theory; and
f) causing a signal to be output that is indicative of the cumulative amount of heating-induced damage which has occurred to said rotary member.

15. The computer program product of claim 14, wherein said heating parameter is a Fourier constant Fo, with $Fo = 4^*\alpha^* t/S^2$, where t is the length of time for which the rotary member is subject to the given cycle of heat-generating loading and S is the thickness of the rotary member.

* * * * *